United States Patent [19]

Schut et al.

[11] 4,283,410

[45] Aug. 11, 1981

[54] 3-AMINO OR AMIDO-2-(1H-INDOL-3-YL) PROPANOIC ACID DERIVATIVES

[75] Inventors: Robert N. Schut, Edwardsburg, Mich.; Max E. Safdy, Elkhart, Ind.; Enrique Hong, Cerro San Francisco, Mexico

[73] Assignee: Miles Laboratories, Inc., Elkhart, Ind.

[21] Appl. No.: 107,076

[22] Filed: Dec. 26, 1979

Related U.S. Application Data

[63] Continuation-in-part of Ser. No. 915,735, Jun. 15, 1978, abandoned.

[51] Int. Cl.$^3$ .................. A61K 31/405; E07D 209/20
[52] U.S. Cl. ............ 424/274; 260/326.13 B; 260/326.14 A; 260/326.14 R; 260/326.14 T
[58] Field of Search ............ 260/326.14 A, 326.14 T, 260/326.14 R, 326.13 B; 424/274

[56] References Cited

PUBLICATIONS

Rozhkov et al., Zh Org. Khim., 12 [5], p. 1076, (1976).

*Primary Examiner*—Donald G. Daus
*Assistant Examiner*—D. B. Springer
*Attorney, Agent, or Firm*—Jerome L. Jeffers

[57] ABSTRACT

Disclosed are compounds characterized by the structural formula:

Various compounds circumscribed by the foregoing formula in which:

R is H, CH$_3$ or CH$_2$CH$_3$,
R' is H, or $$\underset{\text{CCH}_3,}{\overset{\overset{\text{O}}{\|}}{}}$$

X is H, F or OCH$_3$,
Y is H or Cl, and
Z is H or $$\underset{\text{COCH}_2\text{CH}_3}{\overset{\overset{\text{O}}{\|}}{}}$$

are therapeutically useful as anti-hypertensive agents.

23 Claims, No Drawings

3-AMINO OR AMIDO-2-(1H-INDOL-3-YL) PROPANOIC ACID DERIVATIVES

BACKGROUND AND PRIOR ART

This application is a continuation-in-part of co-pending application Ser. No. 915,735, filed June 15, 1978, now abandoned.

Tryptophan, an essential amino acid nutrient having the formula:

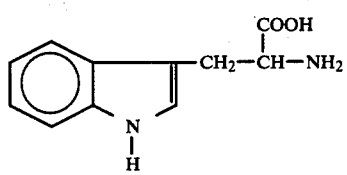

is converted in part by the body into serotonin and melatonin. This later named compound possesses central nervous system activity. Another metabolite of tryptophan, 5-hydroxytryptophan, has been reported by Antonaccio and Robson (J. Pharm. Phrmacol. 25, 495 [1973]) to cause a decrease in blood pressure in monoamine oxidase-inhibited dogs. Another tryptophan derivative, α-methyl-5-hydroxytryptophan ethyl ester, has been reported to lower blood pressure in spontaneously hypertensive rats when given at the extremely large dose of 200 mg/kg (Tabei et al., Eur. J. Pharmacol., 7, 39 [1969]). 5-Fluorotryptophan has been reported to interfere with the synthesis of indole from anthranilic acid and inhibit the growth of E. coli (Bergmann, Proc. Konig. Ned. Akad. Wetenschap, Series C, 57, 108 [1954]).

Rozhkov et al. (Zh. Org. Khim. 12[5], 1076 [1976]) have synthesized the structural isomer of tryptophan, having the structure:

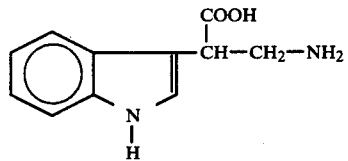

The authors state no utility for this compound.

Johnson et al. have reported that the corresponding α,β-dehydro compound:

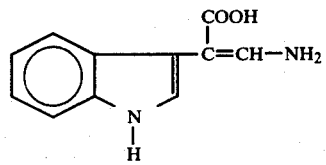

is useful as a chromophore intermediate (Biolumin. Progr. Proc, Kanagawa-ken, Jap. 1965, 67; Chem. Abst. 67;53994K [1967]).

SUMMARY OF THE INVENTION

The present invention involves compounds having the structural formula:

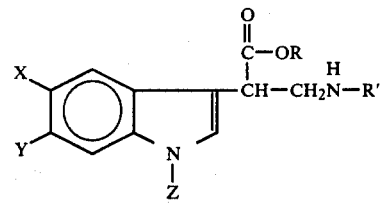

wherein:
R is H, CH$_3$ or CH$_2$CH$_3$,
R' is H or

X is H, F or OCH$_3$,
Y is H or Cl, and
Z is H or

provided that:
(i) when X is F; Y,Z and R' are H and R is H or CH$_3$;
(ii) when Y is Cl; X,Z and R' are H and R is CH$_3$; and
(iii) when X is OCH$_3$; Y is H provided further that when Z and R' are H, R is CH$_3$; when Z is H and R' is

R is H or CH$_3$ and when Z is

R' is

and R is CH$_2$CH$_3$.

Also within the scope of the present invention is the use of the above-described compounds as anti-hypertensive agents.

DETAILED DESCRIPTION OF THE INVENTION

The novel compounds of the present invention are represented by Formula I:

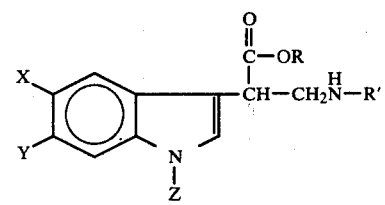

I where the variables X, Y, Z, R and R' are as previously described and qualified. The invention also includes pharmaceutically acceptable, non-toxic, acid addition salts of compounds having Formula I. These salts are prepared from suitable acids, such as hydrochloric, hydrobromic, maleic, fumaric, or the like. The acid addition salts are prepared by reacting compounds of Formula I with at least one equivalent of acid in a water-polar organic solvent mixture, such as water and ethanol.

The compounds and salts of this invention possess unexpected pharmacological properties that render them useful as therapeutic agents for the treatment of hypertension in an individual for whom such therapy is indicated. In the process of lowering blood pressure, the instant compounds produce no tachycardia. The term "individual" means a human being or an experimental animal that is used as a model for a human being. The effective dose may vary from individual to individual, but it is easily determined by one skilled in the art without undue experimentation. Dose forms for the administration of compounds having Formula I may be prepared by recognized methods in the pharmaceutical sciences. Various dose forms of compounds having Formula I may be administered by conventional known methods of therapeutic administration such as oral, intravenous, parenteral, or the like.

The compounds claimed herein are prepared by reacting a compound of Formula II:

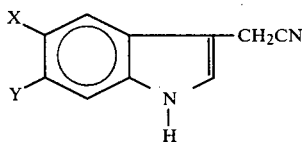

where X and Y are as previously defined and qualified, with an alkali metal base and an appropriate acyloxylating agent to produce a compound having Formula III:

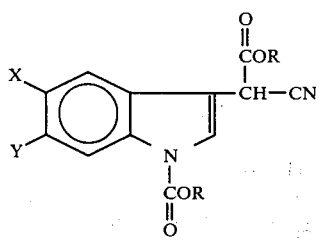

where R is methyl or ethyl. The compound having Formula II where X is fluorine and Y is H is novel, but can be prepared as described in Example 3A, infra. The compound of Formula II where Y is chlorine and X is H is prepared in a similar manner using the 6-chloro rather than the 5-fluoro starting material.

The alkali metal base used in this reaction may be sodium metal, lithium hydride, sodium ethoxide, potassium t-butoxide, or the like. This reaction may be performed in a suitable solvent, such as benzene, dimethylformamide, dimethoxyethane, or the like; or the solvent may be an acyloxylating agent, such as diethyl carbonate or dimethyl carbonate. The acyloxylating agent may be one of the carbonates indicated in the previous sentence, or ethyl chloroformate or methyl chloroformate.

The molar ratios of the compound having Formula II to alkali metal base to acyloxylating agent preferably range from about 1:2:2 to 1:2:10, respectively, with the latter ratio preferred. The preferred reagents are sodium metal and diethyl carbonate, wherein the latter acts as both solvent and acyloxylating agent. The reaction takes place in the temperature range of about 0° C. to 110° C., but it is preferred to have the temperature near 110° C. in order to drive the reaction to completion by distilling off a by-product of the reaction, e.g., ethanol.

The compound having Formula III is hydrogenated to convert the cyano group into an aminomethyl group and produce a compound having the Formula IV:

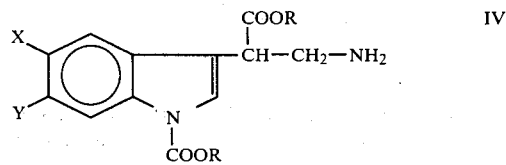

wherein X, Y and R are as previously defined. This reduction is performed under pressure in the presence of a catalyst, such as Raney nickel, Palladium on charcoal, Rhodium on charcoal, or the like. Raney nickel is preferred. The reduction is preferably carried out in a suitable solvent such as methanol, ether, dimethylformamide, or the like at a temperature from about 15° C. to 60° C. Certain acylating agents may act as solvents also, as further described below.

It should be noted that certain undesirable side reactions may occur during the hydrogenation step above. These side reactions can be avoided by protection of the amine group with an acylating agent. The hydrogenated compound above reacts with an acylating agent to produce the N-acylated compound having Formula V:

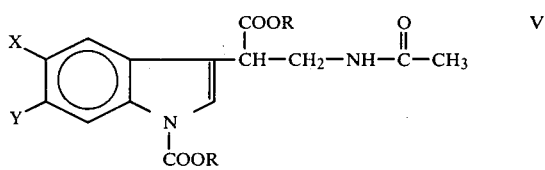

where X, Y and R are as above.

Certain N-acylated compounds have been found to be effective anti-hypertensive agents without reconversion to the amine. The acylation is performed by reacting a compound having Formula IV with an acylating agent, such as acetyl chloride or acetic anhydride in a solvent such as ether, dimethylformamide, acetic anhydride, or the like, at a temperature from about 0° to about 60° C.

It should be recognized by those skilled in the art that if acylation is required for protection then the separate reactions of hydrogenation and acylation can also be accomplished in one step. For example, our preferred mode combines the hydrogenation and acylation reactions and most preferably utilizes acetic anhydride as both the solvent for hydrogenation and the acylating agent.

The compound having Formula V can then be hydrolyzed to produce an alkali salt having the Formula VI:

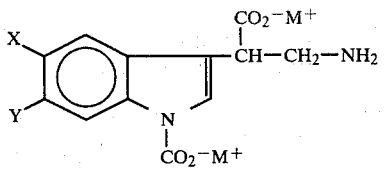

wherein M is an alkali metal cation, with an aqueous solution of an alkali metal hydroxide, such as sodium hydroxide, potassium hydroxide, barium hydroxide, or the like, at a concentration from about 3 N to 10 N for about 1 to 15 hours, at a temperature from about 50° C. to 100° C. The salt is not isolated, but is then promptly decarboxylated to the free acid having Formula I wherein R and Z are hydrogen by addition of an aqueous acid, such as hydrochloric acid, sulfuric acid, or the like. The compound having Formula I wherein R and Z are hydrogen is isolated, after the acidic solution is neutralized, filtered and concentrated.

The hydrolysis of Compound V under mild conditions, i.e., room temperature and the use of 1 N alkali metal hydroxide, results in a partially hydrolyzed compound, illustrated by Formula VII, after acidification:

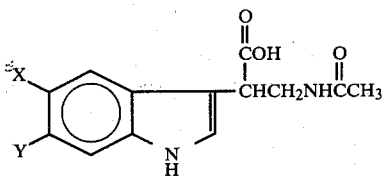

where X and Y are as defined above.

The compound having Formula I, wherein R is hydrogen, can then be esterified by reacting it with methanol in the presence of an acid catalyst, such as hydrochloric acid, sulfuric acid, sulfonyl chloride or the like, and the product, having Formula I, wherein R is methyl, is isolated by convenient means such as crystallization.

The preparation of the novel compounds of the present invention and their utility as anti-hypertensive agents is further illustrated by the following examples.

EXAMPLE 1

This example illustrates the preparation of methyl 3-amino-2-(5-methoxy 1H-indol-3-yl) propanoate and also describes the preparation of intermediates.

A. Ethyl 2-cyano-2-(1-ethoxycarbonyl-5-methoxy-1H-indol-3-yl)acetate (Compound 1A)

A vigorously stirred solution of 5-methoxyindole-3-acetonitrile (22.7 g, 0.13 mole; prepared as described by JUBY and HUDYMA, J. Med. Chem. 12, 396 [1969]) in 200 ml of diethylcarbonate was heated at 110° C. and sodium (6.0 g, 0.26 mole) was added in small pieces over a 30 minute period, during which time ethanol distilled off. The mixture was kept at 110° C. for an additional 60 minutes, and the excess solvent removed in vacuo. The remaining mixture was cooled to about 20° C. and a dilute solution of acetic acid (18 ml glacial acetic acid in 100 ml of water) was added thereto. Then 200 ml of ethyl acetate was added, and the mixture stirred until all solids had dissolved. The organic portion of this mixture was separated, washed with brine, dried over $MgSO_4$, and the solvent evaporated in vacuo to leave a dark residue. This residue was chromatographed on Silica Gel 60 with benzene:ethyl acetate (9:1 v:v) solvent and the solvent evaporated in vacuo to isolate Compound 1A as a light yellow syrup. The product was crystallized from methanol; yield 20 g (47% theory), mp 81°–83° C.

Anal. Calcd. for $C_{17}H_{18}N_2O_5$: C, 61.81; H, 5.49; N, 8.48. Found: C, 62.37; H, 5.58; N, 8.55.

B. Ethyl 3-acetylamino-2-(1-ethoxycarbonyl-5-methoxy-1H-indol-3-yl)propanoate (TR-3328)

A solution of Compound 1A, prepared above, (7.4 g, 0.022 mole) in 150 ml of acetic anhydride was hydrogenated for 20 hours at 50 psi, using about 10 g of Raney nickel as a catalyst. The catalyst was then removed by filtration, and the solvent was evaporated in vacuo to leave a thick syrup. This syrup was dissolved in 200 ml of ethyl acetate which was then washed five times with 6% aqueous potassium carbonate solution and dried over $MgSO_4$. The solvent was then evaporated in vacuo, and the syrup which remained was crystallized from ethyl acetate:petroleum ether. One recrystallization from the same solvent pair yielded 4.6 g (56% theory) of product, mp. 88°–90° C.

Anal. Calcd. for $C_{19}H_{24}N_2O_6$: C, 60.62; H, 6.43; N, 7.44. Found: C, 60.93; H, 6.70; N, 7.87.

C. 3-Amino-2-(5-methoxy-1H-indol-3-yl)propanoic acid (TR-3361)

A mixture of TR-3328 (5.3 g, 0.014 mole; prepared in Part 1B above) and 18 ml of 10 N NaOH was heated at reflux temperature for 8 hours. The mixture was diluted with 100 ml of water, powdered charcoal was added, and the resulting mixture stirred and filtered to produce a clear filtrate. The filtrate was acidified to pH 6.0 with acetic acid, diluted to 200 ml with water, heated to boiling, treated with powdered charcoal, filtered, concentrated in vacuo until solid material was seen, and cooled at about 4° C. for 16 hours. The solid was then removed by filtration, recrystallized from water, and dried over $P_2O_5$; yield 2.1 g (64% theory), mp 205°–207° C. dec.

Anal. Calcd. for $C_{12}H_{14}N_2O_3$: C, 61.52; H, 6.02; N, 11.96. Found: C, 60.58; H, 6.27; N, 11.82

D. Methyl 3-Amino-2-(5-methoxy-1H-indol-3-yl)propanoate Hydrochloride (TR-3369)

A stirred suspension of TR-3361 (1g, 0.0043 mole, prepared in Part 1C, above) in 8 ml of methanol was cooled to −10° C. and $SOCl_2$ (0.4 ml, 0.0056 mole) was added dropwise to generate a clear yellow solution. This solution was stirred for 18 hours at 18° C., and the solvent was then removed in vacuo to leave a gummy residue which turned into a solid upon trituration with ethyl acetate. The residue was partitioned between ethyl acetate and 6% $K_2CO_3$ solution. The organic phase was washed once with brine, dried over $MgSO_4$, and 1.1 ml of 4 N HCl (in dioxane) was added to produce a precipitate. The solid was removed by filtration and dried over $P_2O_5$ to yield 0.8 g product (67% theory), mp.

Anal. Calcd. for $C_{13}H_{17}N_2O_3Cl$: C, 54.83; H, 6.02; N, 9.84; Cl, 12.45. Found: C, 54.36; H, 6.23; N, 9.54 Cl, 12.21.

EXAMPLE 2

This example describes the preparation of 2-(5-methoxy-1H-indol-3-yl)-3-acetamido propanoic acid. (TR-3350)

A mixture of TR-3328, prepared as in Example 1A, (2.5 g, 0.006 mole) and 20 ml of 1 N KOH in methanol (freshly prepared) was stirred at room temperature. After two hours the clear solution was evaporated in vacuo. The residue was takn up in 15 ml of water and filtered. Acidification with 1 N $H_2SO_4$ to pH 3 gave 1.5 g of the desired compound, mp. 97°–99° C.

Anal. Calcd. for $C_{14}H_{16}N_2O_4$: C, 60.86; H, 5.84; N, 10.14. Found: C, 60.33; H, 6.28, N, 9.89.

The 1-methyl ester of TR-3350 is prepared by the acetylation of TR-3369.

EXAMPLE 3

This example describes the preparation of 3-amino-2-(5-fluoroindol-3-yl)propanoic acid and its intermediates.

A. 5-Fluoroindole-3-acetonitrile

A mixture of 38 g of 3-dimethylaminomethyl-5-fluoroindole (0.198 mole; cf. Hoffman et al. J. Heterocyclic Chem. 2, 298 [1965]; of the 5-fluorogramine therein) in 500 ml of methanol was prepared. Then a solution of 25.7 g of KCN (0.396 mole) in 50 ml of water was added, with stirring. The stirred mixture was cooled to 20° C. and 34.6 ml of methyl iodide (0.556 mole) was added over a 20 minute period. The mixture was then stirred about 20° C. for 16 hours. The solvent was removed by evaporation and the residue was partitioned between ether and water. The ether portion was washed with water, 5% HCl, saturated $NaHCO_3$ solution, water, and brine, dried over $MgSO_4$ and evaporated to leave a liquid residue. This residue was distilled at reduced pressure in a Kugelrohr apparatus. The fraction distilling at 134°–140° C. and 0.3 to 0.1 Torr was collected and crystallized from ethyl acetate-petroleum ether, mp. 58°–59°, yield 5.3 g (44% theory).

B. Ethyl 2-cyano-2-(1-ethoxycarbonyl-5-fluoroindol-3-yl) acetate (Compound 3B)

A stirred solution of 5-fluoroindole-3-acetonitrile (15.3 g; 0.88 mole; prepared in Part 3A above) in 250 ml of diethylcarbonate was heated at 110° C. and sodium (4.0 g; 0.17 mole) was added in small pieces. The mixture was then kept at 110° C. for an additional 30 minutes, during which time ethanol distilled off. The excess solvent and ethanol was then removed in vacuo. The residue that remained was cooled and to it was added a dilute solution of acetic acid (25 ml of glacial acetic acid in 100 ml of water). This aqueous mixture was extracted with two 100 ml portions of ether, which were combined, dried over $MgSO_4$ and evaporated to leave a syrup. This syrup crystallized when triturated with methanol. The yield of product was 17 g (61% theory).

C. Ethyl 3-acetylamino-2-(1-ethoxycarbonyl-5-fluoroindol-3-yl)propanoate (Compound 3C)

A solution of Compound 3B, (17 g, 0.054 mole; prepared in Part 3B above) in 250 ml of acetic anhydride was hydrogenated as in Example 1B, and the crystalline product isolated following the procedure therein. The product melted at 120°–121° C., the yield was 9 g (46% theory).

Anal. Calcd. for $C_{18}H_{21}FN_2O_5$: C, 59.32; N, 7.69; H, 5.81. Found: C, 59.05; N, 7.54; H, 5.82.

D. 3-Amino-2-(5-fluoro-1H-indol-3-yl)propanoic acid (TR-3913)

A 4.5 g (0.017 mole) sample of the Compound 3C, prepared in Part 3C above, was hydrolyzed as described in Example 1C above. Isolation of the crystalline product (2 g (72% theory), mp. 244°–245° C.) was accomplished by the procedure therein.

Anal. Calcd. for $C_{11}H_{11}FNO_2$: C, 59.46; H, 4.99; N, 12.61 Found: C, 58.67; H, 4.96; N, 12.89.

EXAMPLE 4

Preparation of methyl 3-amino-2-(5-fluoro-1H-indol-3-yl) propanoate hydrochloride (TR-3915).

The methyl ester of TR-3913 was prepared as described in Example 1D, except TR-3913 (1.6 g, 0.007 mole) was utilized in place of TR-3361 and 0.74 ml of thionyl chloride (0.010 mole) was used. TR-3915, mp 186°–187° C., was isolated in 63% yield (1.2 g).

Anal. Calcd. for $C_{12}H_{14}FN_2O_2Cl$: C, 52.85; H, 5.17; N, 10.27 Found: C, 52.71; H, 5.16; N, 10.04

EXAMPLE 5

This example illustrates the preparation of methyl 3-amino-2-(6-chloro-1H-indol-3-yl)propanoate hydrochloride and also describes the preparation of its intermediates.

A. Ethyl 2-cyano-2-(1-ethoxycarbonyl-6-chloro-1H-indol-3-yl)acetate (Compound 5A)

Sodium (4.8 g, 0.208 mole) was added to 240 ml of absolute ethanol. The reaction vessel was gently warmed in an oil bath and the reaction mixture stirred until all of the Na dissolved. An aspirator was attached to the system and the ethanol gently distilled off to a muddy cake consistency. The heat was removed and the flask allowed to cool to room temperature. A solution of 6-chloroindole-3-acetonitrile (20 g, 0.104 mole), prepared as described by Tuby and Hudyma, J. Med. Chem. 12, 396 (1969) in 200 ml of diethylcarbonate was rapidly added with stirring. The mixture was exothermic initially but then cooled off. Toluene (100 ml) was added and the oil bath brought to 140°–150° C. Distillation began at a temperature of 80° C. After distillation had begun, toluene was added in aliquots to replenish the volume distilled off. When all the ethanol was distilled off the excess solvent was removed in vacuo. The remaining mixture was cooled to about 20° C. and a dilute solution of acetic acid (18 ml glacial acetic acid in 100 ml of water) was added thereto. Then 200 ml of ethanol was added and the mixture stirred until all solids had dissolved. The organic portion of this mixture was separated, washed with brine, dried over $MgSO_4$ and the solvent evaporated in vacuo to leave a dark residue. This residue was mixed with methanol and crystallization occurred. The product was recrystallized from methanol; 18.6 g (53% theory) mp. 126°–128° C. TLC using benzene:acetone (4:1) showed 1 spot. NMR in δμ DMSO and IR in KCl correlated with the title compound.

B. Ethyl 3-acetylamino-2-(1-ethoxycarbonyl-6-chloro-1H-indol-3-yl)propanoate (Compound 5B)

A solution of 5A, prepared above (5 g, 0.015 mole) in 150 ml of acetic anhydride was hydrogenated for 20 hours at 50 psi using about 10 g of Raney nickel as a catalyst. The catalyst was then removed by filtration, and the solvent evaporated in vacuo to leave a thick syrup. This syrup was dissolved in 200 ml of ethyl acetate which was then washed three times with 6% aqueous potassium carbonate solution and dried over $MgSO_4$. The solvent was then evaporated in vacuo and the syrup remaining was crystallized from ethyl acetate: hexane. Yield 4.1 g (72% theory), mp. 138°–140° C.

Anal. Calcd. for $C_{18}H_{21}ClN_2O_5$: C, 56.89; H, 5.57; N, 7.37; Cl, 9.33. Found: C, 56.67; H, 5.71; N, 7.27; Cl, 9.04

C. Preparation of 3-Amino-2-(6-chloro-1H-indol-3-yl) propanoic acid (Compound 5C)

A stirred suspension of 5B, prepared above (5 g, 0.013 mole) and 22 ml of 3 N NaOH was heated at reflux temperature for 20 hours. The mixture was diluted with 100 ml of water, whereupon powdered charcoal was added and the mixture stirred and filtered to produce a clear filtrate. The filtrate was acidified to pH 5 with concentrated HCl diluted to 200 ml with water, concentrated in vacuo until solid material was seen, and cooled at about 4° C. for 16 hours. The solid was then removed by filtration and dried at 55° C. Yield 2.4 g (78% theory), mp. 245°–247° C.

Anal. Calcd. for $C_{11}H_{11}ClN_2O_2$: C, 55.35; H, 4.65; N, 11.74. Found: C, 54.83; H, 4.68; N, 11.52.

D. Preparation of Methyl 3-Amino-2-(6-chloro-1H-indol-3-yl) propanoate hydrochloride (TR-3416)

A stirred suspension of 5 C (4.1 g, 0.017 mole), prepared above, in 40 ml of methanol was cooled to −10° C. and $SOCl_2$ (1.6 ml, 0.022 mole) was added dropwise to generate a clear pink solution. This solution was stirred 18 hours at 18° C. and the solvent was then removed in vacuo to leave a pinkish solid, triturated with ethyl acetate and allowed to stand in the cold. After several hours precipitation of a solid occurred. The solid was removed by filtration and dried at 60° C. Yield 5.1 g (99% theory) mp. 240°–242° C.

Anal. Calcd. for $C_{12}H_{14}N_2O_2Cl_2$: C, 49.84; H, 4.88; N, 9.69; Cl, 24.52. Found: C, 49.82; H, 4.96; N, 9.64; Cl, 24.21.

EXAMPLE 6

Pharmacological Evaluation

This example describes the results obtained when the compounds of this invention and reference compounds were tested for their ability to lower blood pressure in hypertensive rats.

Rats were made hypertensive by applying a figure-of-eight ligature to one kidney and removing the other kidney two weeks later. At least four weeks elapsed after the second operation, before experimental studies were performed. Indirect systolic blood pressure measurements were made with an occluding cuff and pulse sensor system fitted to the rats' tail. Control blood pressure measurements were made before any compounds were administered. Blood pressure measurements were then made 1, 2, 4, 6, and 8 hours after the oral administration of the test compounds at the dose level of 10 mg/kg. Statistical significance of differences between control and post-treatment values was determined by Wilcoxon's signed rank test (F. Wilcoxon and R. A. Wilcox, Some Rapid Approximate Statistical Procedures, Lederle Laboratories, Pearl River, 1964).

Those compounds in Table I which conform to Formula I, supra and whose preparation is not described herein can be prepared according to the general method set out herein. Those compounds of Table I in which R' and R" are methyl are prepared by catalytic hydrogenation in the presence of methanol and formaldehyde. Compound TR-3634, which is 2-methyl substituted, is prepared by the foregoing procedure except that starting Compound II bears a 2-methyl group. Likewise, those compounds which contain a 4-chloro group are prepared by starting with Compound II except that it is chloro substituted in the 4- rather than the 6-position.

The results of the tests are given in Table I below where n signifies the number of rats tested:

TABLE I

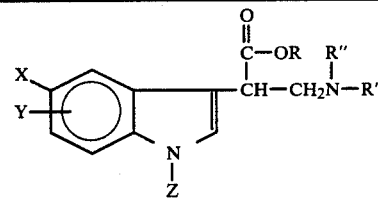

| Compound | X | Y | Z | R | R' | R" | n | 1 hr. | 2 hr. | 4 hr. | 6 hr. | 8 hr. |
|---|---|---|---|---|---|---|---|---|---|---|---|---|
| TR-3257 | H | H | H | H | H | H | 10 | −6 | −8 | −10 | −13 | −8 |
| TR-3264 | H | H | $COOCH_2CH_3$ | $CH_2CH_3$ | $COCH_3$ | H | 10 | −3 | −3 | −18* | −22 | −18 |
| TR-3274 | H | H | H | $CH_3$ | H | H | 10 | −7 | −9 | −9 | −6 | −7 |
| TR-3361 | $OCH_3$ | H | H | H | H | H | 5 | −1 | −10 | +2 | −6 | −2 |
| TR-3398 | H | 6-Cl | $COOCH_2CH_3$ | $CH_2CH_3$ | $COCH_3$ | H | 10 | −18 | −12 | −12 | −7 | −3 |
| TR-3381 | H | 4-Cl | $COOCH_2CH_3$ | $CH_2CH_3$ | $COCH_3$ | H | 10 | −18 | −12 | −12 | −7 | −3 |
| TR-3328[1] | $OCH_3$ | H | $COOCH_2CH_3$ | $CH_2CH_3$ | $COCH_3$ | H | 10 | −15* | −12 | −21* | −20* | −14 |
| TR-3369[1] | $OCH_3$ | H | H | $CH_3$ | H | H | 10 | −85* | −71* | −38* | −10 | +2 |
| (TR-3369 at 3 mg/kg) | | | | | | | 10 | −43* | −36* | −18* | 0 | −3 |
| TR-3395 | H | 4-Cl | H | $CH_3$ | H | H | 10 | −7 | −9 | −20 | −9 | −8 |
| TR-3350[1] | $OCH_3$ | H | H | H | $COCH_3$ | H | 10 | −16 | −18 | −24* | −28* | −8 |
| TR-3404 | H | 6-Cl | H | H | H | H | 5 | −4 | −5 | −14 | −9 | — |
| TR-3416[1] | H | 6-Cl | H | $CH_3$ | H | H | 10 | −14 | −23 | −17* | −15 | −7 |
| TR-3468 | $OCH_3$ | H | H | $CH_3$ | $CH_3$ | $CH_3$ | 5 | −9 | −2 | +1 | +14 | +13 |
| TR-3913[1] | F | H | H | H | H | H | 10 | −19* | −26* | −27* | −15 | 0 |
| TR-3915[1] | F | H | H | $CH_3$ | H | H | 10 | −28* | −18* | −9 | −4 | −1 |

TABLE I-continued

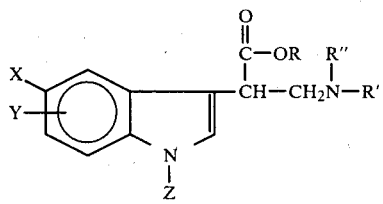

| Compound | X | Y | Z | R | R' | R'' | n | 1 hr. | 2 hr. | 4 hr. | 6 hr. | 8 hr. |
|---|---|---|---|---|---|---|---|---|---|---|---|---|
| TR-3469 | OCH$_3$ | H | H | C$_5$H$_{11}$ | H | H | 5 | −7 | −11 | −3 | −11 | −4 |
| TR-3634[2] | OCH$_3$ | H | H | CH$_3$ | H | H | 5 | +2 | −2 | −8 | −8 | −3 |
| TR-3306 | H | H | H | CH$_3$ | CH$_3$ | CH$_3$ | 5 | −2 | 0 | +2 | +11 | +1 |

*Statistically significant
[1]Compounds claimed herein
[2]2-methyl substituted

Two additional compounds, 5-hydroxy tryptophan (TR-3322) and α-methyl-5-hydroxy tryptophan ethyl ester (TR-3467) were tested for anti-hypertensive activity on 10 rats as described above. The results of these test are as follows:

| | Δ Rat Blood Pressure -mm/Hg | | | | |
|---|---|---|---|---|---|
| Compound | 1 hr. | 2 hr. | 4 hr. | 6 hr. | 8 hr. |
| TR-3322 | −9 | −6 | 0 | +6 | −1 |
| TR-3467 | −2 | −7 | +14 | +22* | +6 |

What is claimed is:

1. 3-Amino or amido-2-(1H-indol-3-yl)propanoic acid compounds characterized by the formula:

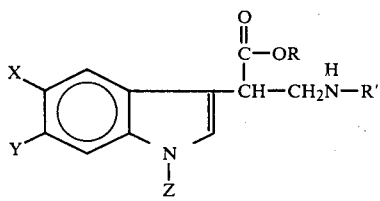

wherein:
R is H, CH$_3$ or CH$_2$CH$_3$,
R' is H or

X is H, F or OCH$_3$,
Y is H or Cl, and
Z is H or

provided that:
(i) when X is F; Y, Z and R' are H and R is H or CH$_3$;
(ii) when X is H, Y is Cl, Z is H, R is CH$_3$ and R' is H; and
(iii) when X is OCH$_3$; Y is H provided further that when Z and R' are H, R is CH$_3$; when Z is H and R' is

R is H and when Z is $$\overset{O}{\underset{\|}{C}}OCH_2CH_3,$$

R' is

and R is CH$_2$CH$_3$.

2. The compounds defined by claim 1 in the form of their pharmaceutically acceptable, non-toxic, acid addition salts.

3. A compound as defined by claim 1 wherein X is OCH$_3$, Y is H, Z is $$\overset{O}{\underset{\|}{C}}OCH_2CH_3,$$

R is CH$_2$CH$_3$ and R' is $$\overset{O}{\underset{\|}{C}}CH_3.$$

4. A compound as defined by claim 1 wherein X is OCH$_3$, Y is H, Z is H, R is CH$_3$ and R' is H.

5. The hydrochloric acid addition salt of the compound defined by claim 4.

6. A compound as defined by claim 1 wherein X is OCH$_3$, Y is H, Z is H, R is H and R' is $$\overset{O}{\underset{\|}{C}}CH_3.$$

7. A compound as defined by claim 1 wherein X is H, Y is Cl, Z is H, R is CH$_3$ and R' is H.

8. The hydrochloric acid addition salt of the compound defined by claim 7.

9. A compound as defined by claim 1 wherein X is F, Y is H, Z is H, R is H and R' is H.

10. A compound as defined by claim 1 wherein X is F, Y is H, Z is H, R is CH₃ and R' is H.

11. The hydrochloric acid addition salt of the compound defined by claim 10.

12. Methyl 3-amino-2-(5-methoxy-1H-indol-3-yl) propanoate hydrochloride.

13. A method of treating hypertension in an individual requiring such treatment which method comprises administering to such individual an anti-hypertensive amount of a compound of the formula:

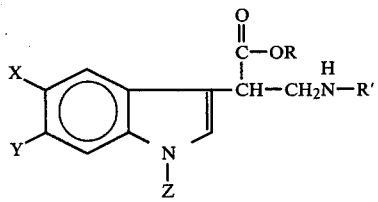

wherein:
R is H, CH₃ or CH₂CH₃,
R' is H or

X is H, F or OCH₃,
Y is H or Cl, and
Z is H or

provided that:
(i) when X is F; Y, Z and R' are H and R is H or CH₃;
(ii) when X is H, Y is Cl, Z is H, R is CH₃ and R' is H; and
(iii) when X is OCH₃; Y is H provided further that when Z and R' are H, R is CH₃, when Z is H and R' is

R is H and when Z is

R' is

and R is CH₂CH₃.

14. The method of claim 13 wherein the compound administered is in the form of its pharmaceutically acceptable, non-toxic, acid addition salt.

15. The method of claim 13 wherein the compound administered is further defined in that X is OCH₃, Y is H, Z is

R is CH₂CH₃ and R' is

16. The method of claim 13 wherein the compound administered is further defined in that X is OCH₃, Y is H, Z is H, R is CH₃ and R' is H.

17. The method of claim 16 wherein the compound defined therein is administered in the form of its hydrochloric acid addition salt.

18. The method of claim 13 wherein the compound administered is further defined in that X is OCH₃, Y is H, Z is H, R is H and R' is

19. The method of claim 13 wherein the compound administered is further defined in that X is H, Y is Cl, Z is H, R is CH₃ and R' is H.

20. The method of claim 19 wherein the compound defined therein is administered in the form of its hydrochloric acid addition salt.

21. The method of claim 13 wherein the compound administered is further defined in that X is F, Y is H, Z is H, R is H and R' is H.

22. The method of claim 13 wherein the compound administered is further defined in that X is F, Y is H, Z is H, R is CH₃ and R' is H.

23. The method of claim 22 wherein the compound defined therein is administered in the form of its hydrochloric acid addition salt.

* * * * *